US009155773B2

(12) United States Patent
Kim et al.

(10) Patent No.: US 9,155,773 B2
(45) Date of Patent: Oct. 13, 2015

(54) ANTIOBESITY COMPOSITION

(75) Inventors: Min-Young Kim, Taejeon (KR); Hee-Suk Lee, Seoul (KR); Joon-Sik Kim, Taejeon (KR); Jong-Cheon Hahm, Taejeon (KR)

(73) Assignee: ANGIOLAB, INC., Daejeon (KR)

( * ) Notice: Subject to any disclaimer, the term of this patent is extended or adjusted under 35 U.S.C. 154(b) by 197 days.

(21) Appl. No.: 12/059,611

(22) Filed: Mar. 31, 2008

(65) Prior Publication Data

US 2008/0187606 A1 Aug. 7, 2008

Related U.S. Application Data

(63) Continuation-in-part of application No. PCT/KR2006/004049, filed on Oct. 9, 2006, and a continuation-in-part of application No. 10/460,951, filed on Jun. 12, 2003, now Pat. No. 7,485,327, which is a continuation-in-part of application No. PCT/KR01/02148, filed on Dec. 12, 2001.

(30) Foreign Application Priority Data

Oct. 5, 2005 (KR) .................. 10-2005-0093577

(51) Int. Cl.
*A61K 36/282* (2006.01)
*A61K 36/53* (2006.01)
*A61K 36/605* (2006.01)
*A61K 36/82* (2006.01)
*A23L 1/30* (2006.01)
*A61K 36/258* (2006.01)
*A61K 36/68* (2006.01)

(52) U.S. Cl.
CPC .............. *A61K 36/82* (2013.01); *A23L 1/3002* (2013.01); *A61K 36/258* (2013.01); *A61K 36/282* (2013.01); *A61K 36/53* (2013.01); *A61K 36/605* (2013.01); *A61K 36/68* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,419,349 A | 12/1983 | Kojima et al. | |
| 6,060,061 A | 5/2000 | Breton et al. | |
| 6,099,845 A | 8/2000 | Na et al. | |
| 6,153,208 A | 11/2000 | McAtee et al. | |
| 6,261,566 B1 | 7/2001 | Pillai et al. | |
| 6,416,769 B1 | 7/2002 | Vromen | |
| 6,485,756 B1 | 11/2002 | Aust et al. | |
| 2001/0024664 A1 | 9/2001 | Obukowicz et al. | |
| 2003/0072822 A1* | 4/2003 | Ribnicky et al. | 424/740 |
| 2004/0009244 A1* | 1/2004 | Kim et al. | 424/729 |
| 2005/0003026 A1* | 1/2005 | Bok et al. | 424/736 |
| 2006/0280700 A1* | 12/2006 | Isler | 424/53 |

FOREIGN PATENT DOCUMENTS

| | | | |
|---|---|---|---|
| CN | 1089095 A | * | 7/1994 |
| FR | 2622110 | | 4/1989 |
| JP | 02256621 | | 10/1990 |
| JP | 06199647 | | 6/1994 |
| JP | 07196526 | | 8/1995 |
| JP | 08301779 | | 11/1996 |
| JP | 09241142 | | 9/1997 |
| JP | 11049693 | | 2/1999 |
| JP | 11147834 | | 6/1999 |
| JP | 2005-320323 | | 11/2005 |
| KR | 2001066713 A | * | 7/2001 |
| KR | 10-2003-0026939 | * | 4/2003 |
| KR | 10-2003-008525 | | 11/2003 |
| KR | 10-2004-006542 | | 7/2004 |
| KR | 10-2005-007886 | | 8/2005 |
| KR | 10-2006-007025 | | 6/2006 |
| KR | 10-2005-008306 | | 8/2006 |
| WO | WO 0041708 A | * | 7/2000 |

OTHER PUBLICATIONS

An, et al., "Protein Kinase C Receptor Binding Assay for the Detection of Chemopreventive Agents from Natural Products," Natural Product Sciences, 3(1):29-37, 1997.

"Melissa Officinalis." PDR for Herbal Medicines. Ed 1. Montvale, New Jersey: Medical Economics Co., 1998. 967-968.

Chlabicz and Galasinski, "The components of *Melissa officinalis* L. that influences protein biosynthesis in-vitro," J Pharm Pharmacol., 38(11):791-794, 1986.

Asano, et al., "Polyhydroxylated alkaloids isolated from mulberry trees (*Morus alba* L.) and silkworms (*Bombyx mori* L.)," J. Agric. Food Chem., 49(9):4208-4213, 2001.

* cited by examiner

Primary Examiner — Chris R Tate
Assistant Examiner — Deborah Davis
(74) Attorney, Agent, or Firm — Joseph H. Kim; JHK Law

(57) ABSTRACT

The present invention provides an antiobesity composition comprising extract of *Melissa* as an active ingredient, use of *Melissa* extract, and a method for suppressing obesity using the composition.

12 Claims, 7 Drawing Sheets

ANTIOBESITY COMPOSITION

The present application is a continuation-in-part application of PCT/KR2006/004049, filed Oct. 9, 2006, which claims the benefit of priority to KR10-2005-0093577, filed Oct. 5, 2005. The present application is also a continuation-in-part application of U.S. patent application Ser. No. 10/460,951, filed Jun. 12, 2003 (now U.S. Pat. No. 7,485,327, issued Feb. 3, 2009), which is a continuation-in-part application of PCT/KR01/02148, filed Dec. 12, 2001, which claim the benefit of priority to Korean Patent Application Nos. 2000/75488, filed Dec. 12, 2000, 2001/8470, filed Feb. 20, 2001, and 2001/77392, filed Dec. 7, 2001.

TECHNICAL FIELD

The present invention relates to an antiobesity composition comprising extract of *Melissa* as an active ingredient, use of *Melissa* extract, and a method for suppressing obesity using the composition. Also, the present invention relates to an antiobesity composition comprising extract of *Melissa* and extract of *Mori Folium* as active ingredients, use of a mixture of *Melissa* extract and *Mori Folium* extract, and a method for suppressing obesity using the composition. Further, the present invention relates to an antiobesity composition comprising extract of *Melissa*, extract of *Artemisia* and extract of *Mori Folium* as active ingredients, use of a mixture of *Melissa* extract, *Artemisia* extract and *Mori Folium* extract, and a method for suppressing obesity using the composition.

BACKGROUND ART

Obesity is regarded as the worst plague ever in the globe and has been declared as a disease by the World Health Organization in 1997. Increase of overweight and obesity has been continued since 1960', and such tendency hardly ever falls.

In USA, the number of people having overweight or obesity is continuously increasing. At present, 65% and 30% of adults over 20 years old are considered as having overweight and obesity, respectively. Even in developing countries, obesity rates in economically developed regions are no less than those of advanced countries. Currently, the number of people with obesity in USA and Japan is up to about 300 million. Every year, more than 0.3 million people die from obesity and the expenses in connection with obesity are amounted to about $100 billion.

Over the world, the obesity population surges with environmental changes boosted by economic development, modernization, and urbanization. And overweight rate is higher in male population than in female, while obesity rate is generally less in male than female. The obesity rate in children and the young is high in developed countries and advanced countries both.

The currently-used therapies for obesity include dietary therapy, physical activity, behavior therapy, drug therapy, combined therapy surgery (gastrectomy), etc.

Most of foods widely used for controlling obesity are dietary fiber, and some foods that have not been medically proved in their effect are also sold in market.

As antiobesity drugs approved by FDA, the following drugs are now available: Orlistat (brand name: Xenical), Phentermine (brand name: Fastin, Zantryl etc.), and Sibutramine (brand name: Reductil, Meridia, etc.).

Orlistat (Xenical), which has been approved most recently, has an efficacy to prevent absorption of about 30% of fat taken from food, thereby makes reduce body weight. In other sides, Phentermine and Sibutramine have an efficacy to suppress appetite.

Orlistat (Xenical) combines with lipase in digestive tract, then makes reduce the lipolysis in the small intestine thereby prevents absorption of fat. However, undegraded fat remaining in the intestine gives rise to several side effects such as abdominal discomfort or pain, rectal discomfort or pain, fatty or oily stools, vomiting, depression, leg pain, swollen feet, etc. Such side effects may be more severe if more fat are taken.

Phentermine changes the serotonin value in the brain to suppress appetite. But it may raise blood pressure and heart rate and stimulate the central nervous system, which are the same side effects of amphetamine.

Sibutramine can suppress reabsorption of norepinephrine, serotonin and dopamine which are neurotransmitters, thereby induce appetite suppression in brain. However, it may cause a lot of side effects including abdominal pain, anxiety, constipation, depression, headache, insomnia, joint pain, nausea, nervousness, stomachache, etc. Furthermore a recent report that Sibutramine (Reductil) is linked to cardiac death brought up the matter of safety as a critical issue.

Accordingly, an ideal obesity treatment should be able to reduce only body fat selectively without affecting muscles and bones, enable maintaining body weight after successful body weight loss, and first of all, have no side effect caused by long-term administration.

In order to develop antiobesity drugs that can solve the above problems and reduce body fat and body weight simultaneously, the inventors of the present invention studied the antiobesity effects of herbal medicines that have been used for a long time.

With regard to antiobesity effects of herbal medicines, KR 10-2004-0065427 A1 discloses anti-obesity biohealth products containing *Artemisia iwayomogi* oligosaccharide, AIP1 (*Artemisia iwayomogi* Polysaccharide Fraction 1) for improving endocrine physiological metabolism of obesity, and KR 10-2005-83066 A1 describes a food for antibesity comprising *Eucommia-ulmoides* Oliver extract or *Morus-alba Linne* extract.

As a result of arduous studies, a composition comprising extract of *Melissa*, a composition comprising extract of *Melissa* and extract of *Mori Folium*, and a composition comprising extract of *Melissa*, extract of *Artemisia* and extract of *Mori Folium* have remarkable effects on reduction of body weight and body fat, and then completed this invention.

DISCLOSURE

Technical Problem

An object of the present invention is to provide an antiobesity composition comprising extract of *Melissa* as an active ingredient, use of *Melissa* extract, and a method for suppressing obesity using the composition. Another object of the present invention is to provide an antiobesity composition comprising extract of *Melissa* and extract of *Mori Folium* as active ingredients, use of a mixture of *Melissa* extract and *Mori Folium* extract, and a method for suppressing obesity using the composition. Still another object of the present invention is to provide an antiobesity composition comprising extract of *Melissa*, extract of *Artemisia* and extract of *Mori Folium* as active ingredients, use of a mixture of *Melissa* extract, *Artemisia* extract and *Mori Folium* extract, and a method for suppressing obesity using the composition.

Technical Solution

Figure 1:
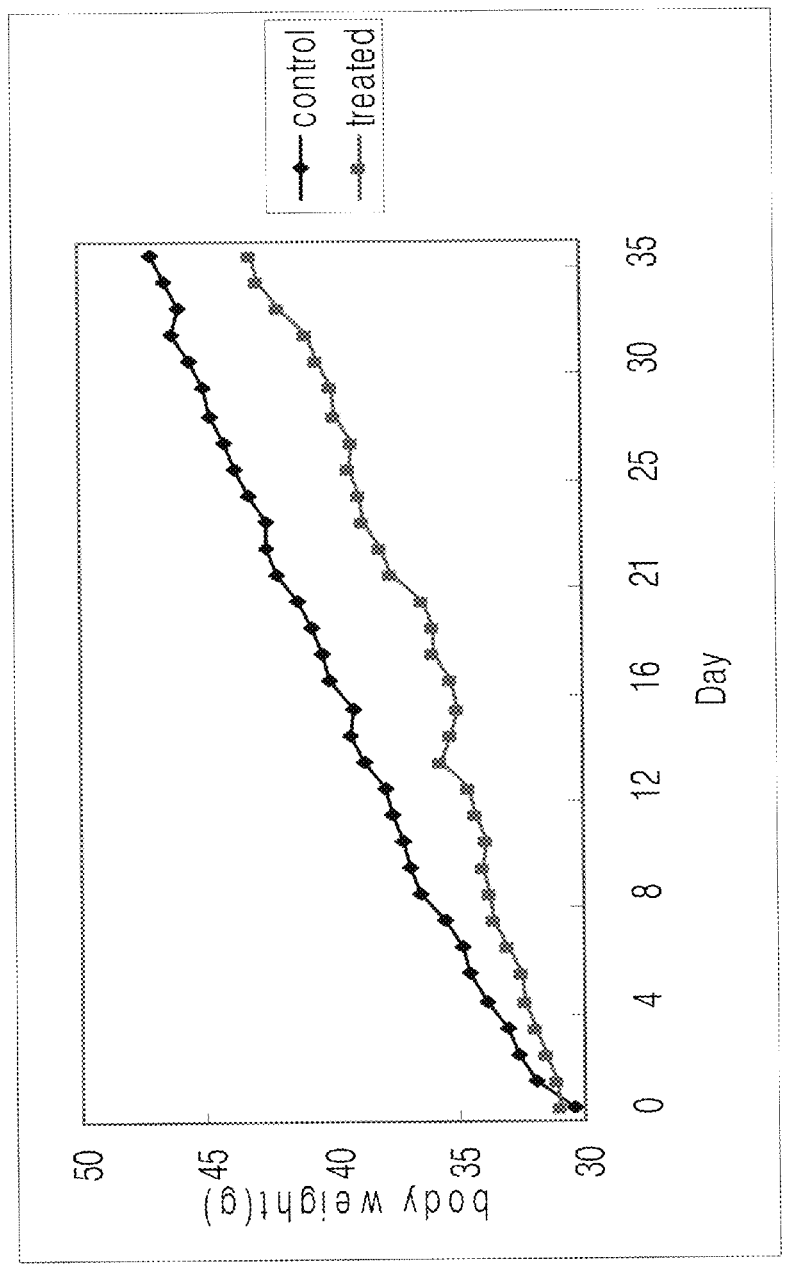
FIG. 1 is a graph showing the reduction of body weight in genetically obese mice with passage of time after administration of the composition of the present invention.

The present invention provides an antiobesity composition comprising extract of *Melissa* as an active ingredient.

In an embodiment of the present invention, said antiobesity composition may comprise extract of *Melissa* of 0.1~100 parts by weight with respect to 100 parts by weight of the composition.

Also, the present invention provides an antiobesity composition comprising extract of *Melissa* and extract of *Mori Folium* as active ingredients.

In an embodiment of the present invention, said antiobesity composition may comprise extract of *Melissa* of 0.1~99 parts by weight and extract of *Mori Folium* 0.1~99 parts by weight, with respect to 100 parts by weight of the composition.

Further, the present invention provides an antiobesity composition comprising extract of *Melissa*, extract of *Artemisia* and extract of *Mori Folium* as active ingredients.

In an embodiment of the present invention, said antiobesity composition may comprise extract of *Melissa* of 0.1~99 parts by weight, extract of *Artemisia* 0.1~99 parts by weight and extract of *Mori Folium* 0.1~99 parts by weight, with respect to 100 parts by weight of the composition.

In another embodiment of the present invention, said composition for antiobesity may comprise extract of *Melissa*, extract of *Artemisia*, extract of *Mori Folium* in the ratio of 1~3:0.1~1:1~3 by dry weight.

The term 'composition' as used hereinbefore or hereinafter is regarded as including any product formed by a mixture of specific ingredients directly or indirectly as well as a product containing the specific ingredients.

'*Melissa*' is a perennial herb in Labitae family, is also called lemon balm, balm, or dropsy plant as common and folk names. Extract of *Melissa* comprises flavonoid, terpene acid, volatile oil, glycosides of alcohol and phenol compound etc., derivatives of caffeic acids and the like. Rosmarinic acid is one of nonvolatile ingredients as a major flavonoide of *Melissa*. It has been known that rosmarinic acid has strong anti-inflammatory and antipyretic property, and essential oil of *Melissa* has abundant medicinal properties particularly for depression, cephalalgia nervosa, decline of memory, neuralgia, pyrexia and the likes. Besides, it has been known that the essential oil of *Melissa* can be applied for sedation, antibacterial, antivirus, antioxidation and antihormone. At present, dry extract of *Melissa* is used as an ingredient of blood circulation promoter.

For the present invention, the term '*Melissa*' may comprise any kind of *Melissa* species including *Melissa officinalis*.

'*Artemisia*' is a perennial herb in Compositae family. It has effects of antipyretic, anti-inflammatory, analgesic, anti-dampness, and has been used for icterus, disturbances of urination, abscess and scabies, and gynecopathy. *Artemisia* comprises several ingredients including scoparone, capillin, capillone, capillene, capillarin etc. Particularly, it has been known that scoparone can make increase secretion of bile and facilitate excretion of bilirubin, ameliorate liver function and can be used for alcohol detoxification, antioxidation, antibacterial and antitumor.

For the present invention, the term '*Artemisia*' may comprise any kind of *Artemisia* species including *Artemisia capillaris*, *Artemisia iwayomogi*, *Artemisia princeps*, *Artemisia annua*, *Artemisia abrotanum*, *Artemisia absinthium*, *Artemisia japonica*, *Artemisia cina*, etc.

'*Mori Folium*' is leaf of *Morus* species, and it has efficacy of prevention of cerebral apoplexy, antipyretic, visual acuity improvement, and can be used for treating of fever, headache, red eye, polydipsia. *Mori Folium* comprises flavonoids including rutin, quercetin, isoquercetin and moracetin; insect metamorphosis hormons including inokosterone, ecdysterone etc. It has been known that extract of *Mori Folium* can be used for hypoglycemic efficacy (KR 10-1998-0021670 A1).

For the present invention, the term '*Mori Folium*' may comprise any kind of leaf of *Morus* species including *Morus alba* L. leaf.

The compositions of the present invention may comprise other antiobesity ingredients as well as one or more of the above herb extracts.

Also, the present compositions may further comprise at least one of materials or ingredients of health care compositions on general standard and norm, including dietary fiber, green tea, ginseng and the likes, or other approved food additives such as vitamin, mineral etc. in appropriate amount.

Said dietary fiber may be at least one of *Psyllium* husk, cellulose, hemicellulose, crystalline cellulose, lignin, pectin, alginic acid, polymanuronic acid, guar gum, arabia gum, arabinogalactan, Konjak mannan, inulin, levan, polydextrose and indigestible maltodextrin.

Said green tea may be green tea powder, green tea extraction liquid or powder of green tea extraction liquid.

Also, said ginseng may be ginseng powder, ginseng extraction liquid or powder of ginseng extraction liquid.

Also, the present composition may further comprise at least one of vitamin such as vitamin A, vitamin $B_1$, vitamin $B_2$, vitamin $B_3$, vitamin $B_6$, vitamin $B_{12}$, folic acid, vitamin C, vitamin $D_3$, vitamin E; minerals such as copper, calcium, iron, magnesium, potassium, zinc, etc., or other approved food additives, in appropriate amount.

The content of the ingredients other than the active ingredients is not particularly limited, however, is generally a range of 0-98 parts by weight with respect to 100 parts by weight of the composition.

In preparing of the present compositions, the herb extracts can be purchased or prepared with conventional methods.

Any of dried, non-dried, or blending of dried and non-dried herbs may be used to extraction process.

A skilled person in the art may use the extract of the above herbs as extraction liquid or powder of extraction liquid. For extraction, the herbs may be dried, dried and sliced, or dried and powdered according to conventional drying method, and then extracted by conventional extraction method, for example, hot water extraction or organic solvent extraction. Commercially available powder of extraction liquid can also be used.

For example, the herb extracts can be prepared by slicing herbs finely, extracting 1~5 times repeatedly the sliced herbs with water, lower alcohol or mixed solvent thereof, or organic solvent in amount of 3-20 fold of the herbs at room temperature to 100☐ for approximately 6 hours~10 days, then filtrating and concentrating in vacuum or lyophilizing the extraction liquid. The extraction may be processed via conventional extraction methods such as cold water maceration extraction, sonication extraction or reflux extraction.

Said lower alcohol may include $C_{1-4}$ alcohol, and said organic solvent may include nonpolar solvents such as ethylacetate, chloroform, hexane and dichloromethane. In order to obtain proper extraction result, it is prefer to use the solvents in amount of more than 3 times of herb. But if the amount of solvents is more than 20-fold of herb, it is likely to overconsume the solvents comparing the amount of extraction.

The composition of the present invention can be used in any form according to the purpose of the composition, for example, a pharmaceutical composition or a nutraceutical composition to reduce body weight and body fat.

The pharmaceutical composition of the present invention can be made in any form such as granule, powder, tablet, coated tablet, capsule, pill, syrup, drop, solution, suspension, and emulsion, or sustained release formulation of the active ingredient(s).

The composition of the present invention may further comprise one or more pharmaceutically or physiologically acceptable carriers to be formulated appropriately for administration. The pharmaceutically or physiologically acceptable carriers can be, for example, saline, autoclaved water, Ringer's solution, buffered saline, dextrose, maltodextrin, glycerol, ethanol, and the mixture thereof. If necessary, the composition of the present invention can comprise conventional additives such as antioxidant, buffer and antiseptic substances. The composition of the present invention can also comprise pharmaceutically and physiologically acceptable additives such as diluent, dispersing agent, surfactant, solvent, disintegrating agent, sweetener, binder, coating agent, blowing agent, lubricant, glidant or flavoring agent. By using conventional methods or the written text of Remington's Pharmaceutical Science (Mack Publishing Company, Easton Pa.), the compositions of the present invention can be formulated in any desirable forms according to disease or ingredient.

The composition of the present invention can be administered via various routes including oral, intravenous, intraarterial, intraperitoneal, intrathoracic, transdermal, nasal, inhalation, topical, rectal, ocular, and subcutaneous introduction, according to conventional method of administration.

The nutraceutical composition of the present invention can take any form of foods. For example, it can be dried with carriers and then be produced as capsule, or processed to tablet, granule, powder, beverage, gruel, etc, according to the conventional methods in the art.

Examples of food comprising the present composition include meat, tea, beverage, snack, confectionery, noodles, candy, chocolate, ice cream, gum, vitamin combination, functional foods, etc.

The present compositions can be used to suppress increase of body weight and body fat for antiobesity.

The present invention provides a method for suppressing obesity which comprises administering an effective amount of an antiobesity composition comprising *Melissa* extract to a subject in need thereof. Also, the present invention provides a method for suppressing obesity which comprises administering an effective amount of an antiobesity composition comprising *Melissa* extract, *Artemisia* extract and *Mori Folium* extract. In these methods, the explanations for the antiobesity compositions are the same as the above.

When the present compositions are administered to genetically obese mice and high fat diet-induced obese mice, for 5 weeks, it can be found body fat and gonadal fat in the mice are decreased. Also, the compositions further comprising supplementary ingredients such as dietary fiber, green tea, ginseng, etc., show synergy effects on antiobesity action such as reduction of body weight and reduction of body fat and gonadal fat.

Also, when the present compositions are administered to genetically obese mice and high fat diet-induced obese mice, blood cholesterol level and obesity-related blood glucose level are decreased.

Further, upon administrating of the present compositions, there is no sign that adipocytes get hypertrophic, instead, size and dimension of fat cells are decreased, and numbers and size of lipid vacuoles in the liver are decreased, thereby accumulation of lipid in the liver decreased.

Furthermore, on human clinical trial, body weight, body fat percentage, visceral fat, apolipoprotin B concentration, the ratio of total cholesterol/HDL cholesterol and the ratio of LDL cholesterol/HDL cholesterol are significantly decreased, and atherogenic index is improved and muscle mass is increased.

The active ingredients of the present invention, extract of *Melissa*, extract of *Artemisia capillaries* and extract of *Mori Folium* themselves have little toxicity and side effects, thus the present composition can be safely administered for a long period.

Upon deciding dosage of the present composition, the daily dosage of extracts of *Melissa, Artemisia*, and *Mori Folium* would be desirably 0.1~200 mg/kg, 0~200 mg/kg and 0~200 mg/kg, respectively. The dosage can be determined by various factors such as the type and severity of patient's symptom, the content of active ingredient, the content and type of other ingredients, the type of formulation, patient's parameters (age, body weight, health status, sex), food, dosing time, administration route, the ratio of composition, time of treatment, and other co-administrated drug.

As described in the above, extract of *Melissa* has outstanding effect on antiobesity, and a mixture comprising extract of *Melissa* and extract of *Mori Folium*, and a mixture comprising extract of *Melissa*, extract of *Artemisia* and extract of *Mori Folium* have superior effect to extract of *Melissa* itself. Thus, the present invention provides a novel use of *Melissa* extract for the manufacture of antiobesity composition, a novel use of a mixture of *Melissa* extract and *Mori Folium* extract for the manufacture of antiobesity composition, and a novel use of a mixture of *Melissa* extract, *Artemisia* extract and *Mori Folium* extract for the manufacture of antiobesity composition. In these use, the description for the composition for antiobesity is same as the above.

In one aspect, the invention is directed to a method for decreasing body fat mass in a subject, identified as in need of a decrease in body fat mass, by administering to the subject a therapeutically effective amount of a composition comprising an extract of *Melissa* and/or optionally an extract of *Mori Folium* or a mixture comprising extract of *Melissa*, extract of *Artemisia* and extract of *Mori Folium*, or any combination thereof.

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

The following examples serve to provide further appreciation of the invention but are not meant in any way to restrict the effective scope of the invention.

EXAMPLES

Example 1

Preparation of the Formulation 1

A capsule comprising an active ingredient was produced as follows.

25 g of extract of *Melissa officinalis* was prepared to a capsule formulation (hereunder as 'sample 1') according to the conventional encapsulation method.

The constituents of the capsule are as follows.

| Extract of *Melissa officinalis* | 25 g |
|---|---|
| Excipients | qs |

Example 2

Preparation of the Formulation 2

A capsule comprising active ingredients was produced as follows.

10 g of extract of *Melissa officinalis*, and 10 g of extract of *Morus alba* L. leaf were mixed, and the mixture was prepared to a capsule formulation (hereunder as 'sample 2') according to the conventional encapsulation method.

The constituents of the capsule are as follows.

| Extract of *Melissa officinalis* | 10 g |
|---|---|
| Extract of *Morus alba* L. leaf | 10 g |
| Excipients | qs |

Example 3

Preparation of the Formulation 3

A capsule comprising active ingredients was produced as follows.

10 g of extract of *Melissa officinalis*, 5 g of extract of *Artemisia capillaris*, and 10 g of extract of *Morus alba* L. leaf were mixed, and the mixture was prepared to a capsule formulation (hereunder as 'sample 3') according to the conventional encapsulation method.

The constituents of the capsule are as follows.

| Extract of *Melissa officinalis* | 10 g |
|---|---|
| Extract of *Artemisia capillaries* | 5 g |
| Extract of *Morus alba* L. leaf | 10 g |
| Excipients | qs |

Example 4

Preparation of the Formulation 4

A liquid formulation comprising active ingredients was produced as follows.

0.1 g of extract of *Melissa officinalis*, 0.05 g of extract of *Artemisia capillaries*, and 0.1 g of extract of *Morus alba* L. leaf were dissolved in distilled water to produce 1000 ml of formulation (hereunder 'sample 4').

| Extract of *Melissa officinalis* | 10 g |
|---|---|
| Extract of *Artemisia capillaries* | 5 g |
| Extract of *Morus alba* L. leaf | 10 g |
| Distilled water | qs |

Example 5

Preparation of the Formulation 5

A formulation comprising active ingredients and dietary fiber was produced as follows.

6 g of extract of *Melissa officinalis*, 4 g of extract of *Artemisia capillaries*, 6 g of extract of *Morus alba* L. leaf, and 84 g of dietary fiber (Konjak mannan, indigestible maltodextrin) were mixed to produce the formulation (hereunder 'sample 5').

| Extract of *Melissa officinalis* | 6 g |
|---|---|
| Extract of *Artemisia capillaries* | 4 g |
| Extract of *Morus alba* L. leaf | 6 g |
| Konjak mannan | 12 g |
| Indigestible maltodextrin | 72 g |

Example 6

Preparation of the Formulation 6

A formulation comprising active ingredients and green tea extract was produced as follows.

6 g of extract of *Melissa officinalis* 4 g of extract of *Artemisia capillaries*, 6 g of extract of *Morus alba* L. leaf, and 84 g of green tea extract (including 20% of catechin) were mixed to produce the formulation (hereunder 'sample 6').

| Extract of *Melissa officinalis* | 6 g |
|---|---|
| Extract of *Artemisia capillaries* | 4 g |
| Extract of *Morus alba* L. leaf | 6 g |
| Green tea extract | 84 g |

Example 7

Preparation of the Formulation 7

A formulation comprising active ingredients and ginseng extract was produced as follows.

6 g of extract of *Melissa officinalis*, 4 g of extract of *Artemisia capillaries*, 6 g of extract of *Morus alba* L. leaf, and 4 g of ginseng extract powder (ginseng content: 110 mg/g) were mixed to produce the formulation (hereunder as 'sample 7').

| | |
|---|---|
| Extract of *Melissa officinalis* | 6 g |
| Extract of *Artemisia capillaries* | 4 g |
| Extract of *Morus alba* L. leaf | 6 g |
| Ginseng extract powder | 4 g |

Comparison Example

Preparation of Formulation Comprising the Extract of *Artemisia* and the Extract of *Mori Folium*

A capsule comprising active ingredients was produced as follows.

5 g of extract of *Artemisia capillaries* and 10 g of extract of *Morus alba* L. leaf were mixed to produce the formulation (hereunder 'comparison sample').

The constituents of a capsule are as follows.

| | |
|---|---|
| Extract of *Artemisia capillaries* | 5 g |
| Extract of *Morus alba* L. leaf | 10 g |

Experimental Example 1

Antiobesity Effect in Genetically Obese Mice (ob/ob Mice)

Antiobesity effects of the above formulation were observed by oral administration to genetically obese mice.

Five-week-old male obese mice (B6.V-Lep<ob>, Jackson Laboratory) were used for the experiment and after a few days of adjustment period, the control group was administered with saline solution while the treatment groups were administered with each sample 1~7 dissolved in saline solution.

For comparison formulation, 25 mg of the comparison sample was dissolved in 10 ml of saline solution, and 0.4 ml of the solution was orally administered to each mouse everyday for 5 weeks, which was designed to contain active ingredient of 50 mg/kg.

For the formulation 1,2 and 3, 25 mg of each sample was dissolved in 10 ml of saline solution and orally administered to mice 0.4 ml per day for 5 weeks, which was designed to contain active ingredient of 50 mg/kg.

For the formulation 4, 40 mg of sample 4 was dissolved in 160 ml of saline solution and supplied to mice as drinking water for 5 weeks, which was designed to contain active ingredients of 40 mg/kg.

For the formulation 5, 1.56 g of sample 5 was suspended in 100 ml of saline solution and orally administered to mice 0.4 ml per day for 5 weeks, which was designed to contain active ingredients of 50 mg/kg.

For the formulation 6, 1.56 g of sample 6 was suspended with 100 ml of saline solution and orally administered to mice 0.4 ml per day for 5 weeks, which was designed to contain active ingredients of 50 mg/kg.

For the formulation 7, 312.5 mg of sample 7 was suspended with 100 ml of saline solution and orally administered to mice 0.4 ml per day for 5 weeks, which was designed to contain active ingredients of 50 mg/kg.

The body weights were measured daily from the day of sample administration and food intake was determined by estimating the amount of food consumed by the mice throughout the treatment period.

After 5 weeks, blood samples were collected to measure blood glucose and animals were sacrificed by cervical dislocation, and adipose tissues were harvested, weighed, snap frozen in liquid nitrogen and stored at $-80°$ C. until use. The results are described in the Table 1 below.

TABLE 1

Antiobesity effect in genetically obese mice (ob/ob mice)

| Sample | Item | Control group | Treatment group | Decrease rate |
|---|---|---|---|---|
| comparison sample | body weight(g) | 47.0 ± 3.85 | 45.1 ± 4.22 | 4% |
| | body weight gain(g) | 16.6 ± 2.24 | 14.4 ± 2.02 | 14% |
| | subcutaneous fat(g) | 1.02 ± 0.15 | 0.95 ± 0.13 | 7% |
| | gonadal fat(g) | 3.24 ± 0.23 | 3.13 ± 0.31 | 4% |
| sample 1 | body weight(g) | 47.0 ± 3.85 | 44.2 ± 3.96 | 6% |
| | body weight gain(g) | 16.6 ± 2.24 | 13.3 ± 2.28 | 20% |
| | subcutaneous fat(g) | 1.02 ± 0.15 | 0.95 ± 0.11 | 7% |
| | gonadal fat(g) | 3.24 ± 0.23 | 3.09 ± 0.30 | 5% |
| sample 2 | body weight(g) | 47.0 ± 3.85 | 43.9 ± 4.21 | 7% |
| | body weight gain(g) | 16.6 ± 2.24 | 13.1 ± 2.98 | 21% |
| | subcutaneous fat(g) | 1.02 ± 0.15 | 0.92 ± 0.15 | 10% |
| | gonadal fat(g) | 3.24 ± 0.23 | 3.04 ± 0.28 | 6% |
| sample 3 | body weight(g) | 47.0 ± 3.85 | 43.1 ± 4.17 | 8% |
| | body weight gain(g) | 16.6 ± 2.24 | 12.1 ± 3.01 | 27% |
| | subcutaneous fat(g) | 1.02 ± 0.15 | 0.87 ± 0.12 | 15% |
| | gonadal fat(g) | 3.24 ± 0.23 | 3.01 ± 0.37 | 7% |
| sample 4 | body weight(g) | 47.0 ± 3.85 | 44.7 ± 4.20 | 5% |
| | body weight gain(g) | 16.6 ± 2.24 | 12.5 ± 2.43 | 25% |
| | subcutaneous fat(g) | 1.02 ± 0.15 | 0.93 ± 0.11 | 9% |
| | gonadal fat(g) | 3.24 ± 0.23 | 3.11 ± 0.42 | 4% |
| sample 5 | body weight(g) | 47.0 ± 3.85 | 42.8 ± 4.31 | 9% |
| | body weight gain(g) | 16.6 ± 2.24 | 11.3 ± 2.01 | 32% |
| | subcutaneous fat(g) | 1.02 ± 0.15 | 0.82 ± 0.12 | 20% |
| | gonadal fat(g) | 3.24 ± 0.23 | 2.92 ± 0.24 | 10% |
| sample 6 | body weight(g) | 47.0 ± 3.85 | 42.8 ± 4.44 | 9% |
| | body weight gain(g) | 16.6 ± 2.24 | 11.8 ± 2.11 | 29% |
| | subcutaneous fat(g) | 1.02 ± 0.15 | 0.83 ± 0.12 | 19% |
| | gonadal fat(g) | 3.24 ± 0.23 | 2.95 ± 0.30 | 9% |
| sample 7 | body weight(g) | 47.0 ± 3.85 | 42.7 ± 4.01 | 9% |
| | body weight gain(g) | 16.6 ± 2.24 | 12.5 ± 1.11 | 25% |
| | subcutaneous fat(g) | 1.02 ± 0.15 | 0.85 ± 0.22 | 17% |
| | gonadal fat(g) | 3.24 ± 0.23 | 2.98 ± 0.28 | 8% |

As shown in Table 1, the treatment group with sample 1 had 6% decrease in average body weight and 20% decrease in body weight gain, especially 7% decrease in subcutaneous fat and 5% decrease in gonadal fat compared to those of control group.

The treatment group with sample 2 had 7% decrease in average body weight and and 21% decrease in body weight gain, especially 10% decrease in subcutaneous fat and 6% decrease in gonadal fat compared to those of control group.

The treatment group with sample 3 had 8% decrease in average body weight and 27% decrease in body weight gain, especially 15% decrease in subcutaneous fat and 7% decrease in gonadal fat compared to those of control group.

When compared the reduction rate of subcutaneous fat for the treatment group with comparison sample comprising extract of *Artemisia* and extract of *Mori Folium*, antiobesity effect of the treatment group with sample 1 and 2 comprising the extract of *Melissa* has enhanced.

Furthermore, it was shown that the composition comprising extract of *Melissa*, extract of *Artemisia* and extract of *Mori Folium* has an outstanding effect of antiobesity that reduces body fat considerably.

Particularly, when sample 3, with its contents of active ingredients remaining, is combined with functional food ingredients such as dietary fiber, green tea, or ginseng, antiobesity effect was increased.

With respect to the decrease of body fat (subcutaneous fat and gonadal fat), on the basis of sample 3, 135% was decreased by the sample 5 which contains dietary fiber, 124% by the sample 6 which contains green tea extract, and 112% by the sample 7 which contains ginseng extract powder, which demonstrated the increase in antiobesity effects.

In addition, the FIG. 1 describes change in body weight for 35-day administration of sample 3, body weight was decreased in the treatment group compared to the control group.

Therefore, it could be verified that the compositions of the present invention were effective in antiobesity by reducing body weight and especially body fat.

Experimental Example 2

Antiobesity Effect in High Fat Diet-Induced Obese Mice

Antiobesity effects of the present compositions were observed in high fat diet-induced obese mice.

Six-week-old male mice (C57BL/6J mouse, Jackson Laboratory) were used for the experiment and high-fat diet (15% [wt/wt] fat) were produced by Oriental Yeast in Japan. After a few days of adjustment period, the control group was fed with high fat diet only, while the treatment groups were fed with high fat diet supplemented with samples 1-7 respectively for 16 weeks.

The body weights were measured daily from the day of sample administration and food intake was determined by estimating the amount of food consumed by the mice throughout the treatment period.

After 16 weeks, blood samples were collected and animals were sacrificed by cervical dislocation, and adipose tissues were harvested, weighed, snap frozen in liquid nitrogen and stored at −80° C. until use. The results are described in the Table 2.

TABLE 2

Antiobesity effect in high fat diet-induced obese mice (C57BL/6J mice)

| Sample | Item | Control group | Treatment group | Decrease rate |
|---|---|---|---|---|
| comparison sample | body weight(g) | 32.2 ± 2.40 | 31.2 ± 2.27 | 3% |
|  | body weight gain(g) | 11.1 ± 2.65 | 10.1 ± 2.58 | 10% |
|  | subcutaneous fat(g) | 0.82 ± 0.20 | 0.70 ± 0.19 | 15% |
|  | gonadal fat(g) | 0.41 ± 0.13 | 0.35 ± 0.12 | 16% |
| sample 1 | body weight(g) | 32.2 ± 2.40 | 30.9 ± 2.07 | 4% |
|  | body weight gain(g) | 11.1 ± 2.65 | 9.7 ± 2.14 | 13% |
|  | subcutaneous fat(g) | 0.82 ± 0.20 | 0.66 ± 0.24 | 20% |
|  | gonadal fat(g) | 0.41 ± 0.13 | 0.35 ± 0.09 | 16% |
| sample 2 | body weight(g) | 32.2 ± 2.40 | 30.9 ± 1.95 | 4% |
|  | body weight gain(g) | 11.1 ± 2.65 | 9.7 ± 2.53 | 13% |
|  | subcutaneous fat(g) | 0.82 ± 0.20 | 0.64 ± 0.18 | 22% |
|  | gonadal fat(g) | 0.41 ± 0.13 | 0.33 ± 0.07 | 20% |
| sample 3 | body weight(g) | 32.2 ± 2.40 | 30.4 ± 1.91 | 6% |
|  | body weight gain(g) | 11.1 ± 2.65 | 9.3 ± 2.89 | 16% |
|  | subcutaneous fat(g) | 0.82 ± 0.20 | 0.62 ± 0.12 | 24% |
|  | gonadal fat(g) | 0.41 ± 0.13 | 0.30 ± 0.06 | 27% |
| sample 4 | body weight(g) | 32.2 ± 2.40 | 30.6 ± 0.28 | 5% |
|  | body weight gain(g) | 11.1 ± 2.65 | 9.7 ± 1.90 | 12% |
|  | subcutaneous fat(g) | 0.82 ± 0.20 | 0.66 ± 0.20 | 19% |
|  | gonadal fat(g) | 0.41 ± 0.13 | 0.33 ± 0.11 | 20% |
| sample 5 | body weight(g) | 32.2 ± 2.40 | 29.9 ± 2.25 | 7% |
|  | body weight gain(g) | 11.1 ± 2.65 | 8.7 ± 1.98 | 21% |
|  | subcutaneous fat(g) | 0.82 ± 0.20 | 0.56 ± 0.21 | 32% |
|  | gonadal fat(g) | 0.41 ± 0.13 | 0.26 ± 0.08 | 37% |
| sample 6 | body weight(g) | 32.2 ± 2.40 | 29.7 ± 2.68 | 7% |
|  | body weight gain(g) | 11.1 ± 2.65 | 9.0 ± 1.57 | 19% |
|  | subcutaneous fat(g) | 0.82 ± 0.20 | 0.58 ± 0.19 | 29% |
|  | gonadal fat(g) | 0.41 ± 0.13 | 0.27 ± 0.11 | 34% |
| sample 7 | body weight(g) | 32.2 ± 2.40 | 30.2 ± 3.21 | 6% |
|  | body weight gain(g) | 11.1 ± 2.65 | 9.2 ± 2.43 | 17% |
|  | subcutaneous fat(g) | 0.82 ± 0.20 | 0.6 ± 0.12 | 27% |
|  | gonadal fat(g) | 0.41 ± 0.13 | 0.3 ± 0.11 | 27% |

The treatment group with sample 1 had 4% decrease in average body weight and 13% decrease in body weight gain, and particularly 20% reduction in subcutaneous fat and 16% in gonadal fat compared to control group.

The treatment group with sample 2 had 4% decrease in average body weight and 13% decrease in body weight gain, and particularly 22% reduction in subcutaneous fat and 20% in gonadal fat compared to control group.

The treatment group with sample 3 had 6% decrease in average body weight and 16% decrease in body weight gain, and particularly 24% reduction in subcutaneous fat and 27% in gonadal fat compared to control group.

These results demonstrated that the compositions of the present invention containing extract of *Melissa* clearly reduced body fat, enhancing antiobesity effect compared to that of comparison sample.

With respect to the reduction of body fat (subcutaneous fat and gonadal fat), on the basis of sample 3, 132% was decreased by sample 5 which contains dietary fiber, 123% by sample 6 which contains green tea extract, and 107% by sample 7 which contains ginseng extract powder, which demonstrated the enhanced antiobesity effects as shown in Experimental Example 1.

Figure 2:
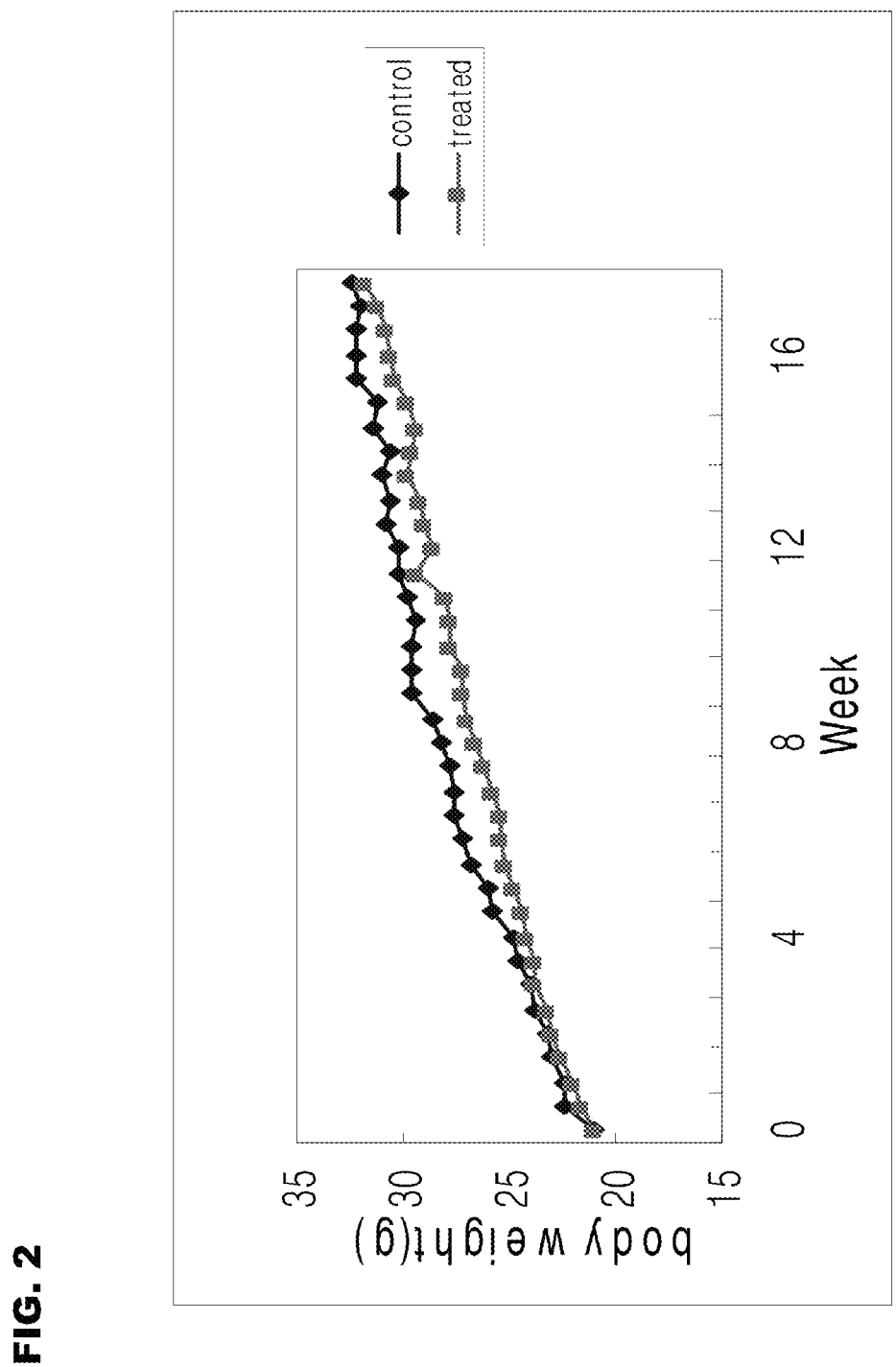
FIG. 2 is a graph showing the reduction of body weight in high fat diet-induced obese mice with passage of time after administration of the composition of the present invention.

Additionally, the FIG. 2, which shows changes in body weight during 16-week administration of sample 3, demonstrates that the body weight increase rate of the treatment group is slower than that of the control group.

Therefore, it could be verified that the compositions of the present invention were effective in antiobesity by reducing body weight, and especially body fat.

Experimental Example 3

Blood and Histological Analysis

With oral administration of the present compositions, changes in blood and tissue in genetically obese mice were analyzed.

First, sample 3 had been administered to genetically obese (ob/ob) mice for 5 weeks and their blood was collected to measure changes in blood cholesterol level.

For histological analysis, subcutaneous fats were cryosected and stained with osmium tetroxide to measure the size and number of adipocytes. Livers were fixed in 4% glutaraldehyde and processed in a routine manner for paraffin section. Sections were cut and stained with 2% osmium tetroxide.

3-1) Analysis of Blood Cholesterol

The blood cholesterol level of the treatment group that was administered with sample 3 was 128±15.2 mg/dl while that of the control group received with saline solution only (vehicle) was 140±17.6 mg/dl. Accordingly, the present composition was found to decrease blood cholesterol by 9%.

3-2) Analysis of Blood Glucose

Figure 3:
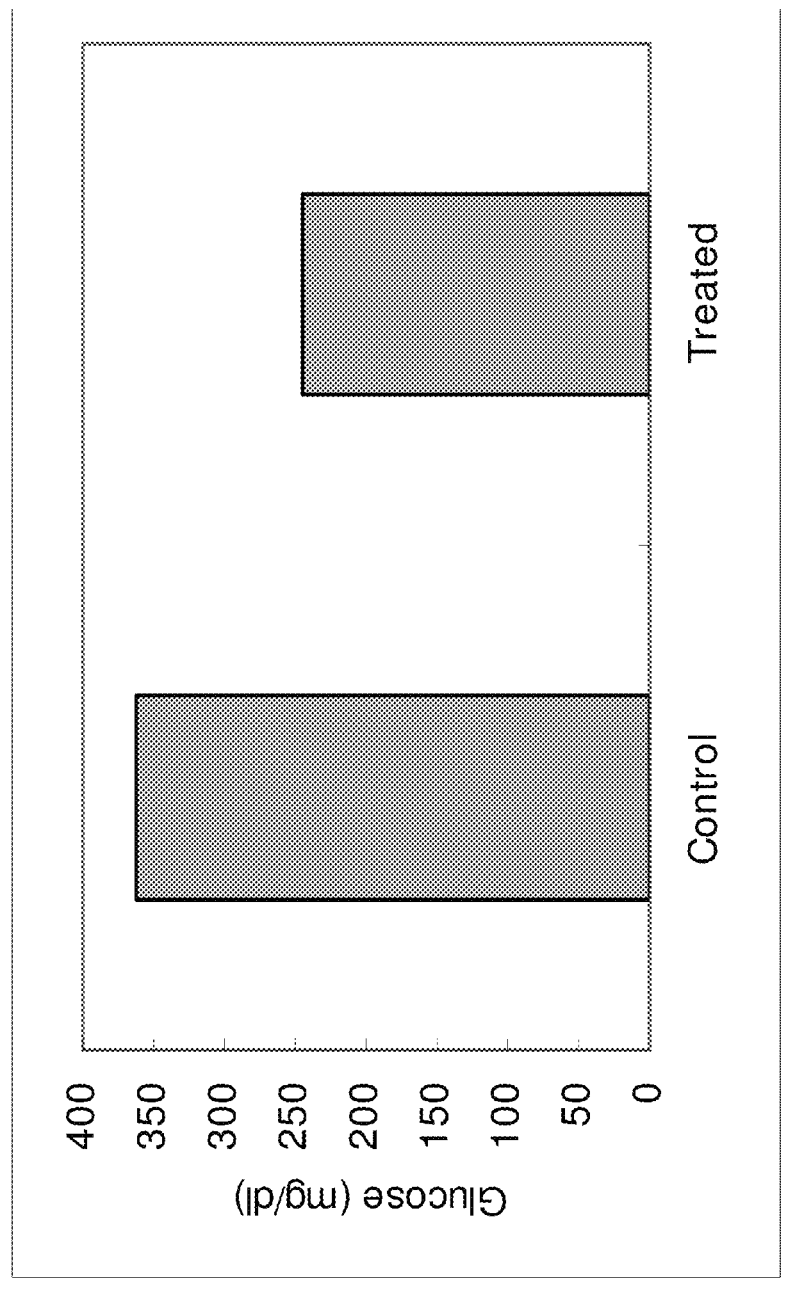
FIG. 3 is a graph showing the effect of the composition of the present invention on the obesity-related blood glucose level.

As shown in the FIG. 3, the blood glucose level of treatment group administered with sample 3 was 244.4±115.2 mg/dl, while that of control group was 362.1±129.7 mg/dl, demonstrating that blood glucose level was decreased by 33% in the treatment group.

Therefore, it was verified that the present composition reduced blood cholesterol level and blood glucose which relates to obesity.

3-3) Histological Analysis of Obese Mice Supplied with the Present Composition

The sizes of subcutaneous adipocytes of control group and treatment group were analyzed after staining.

Figure 4:
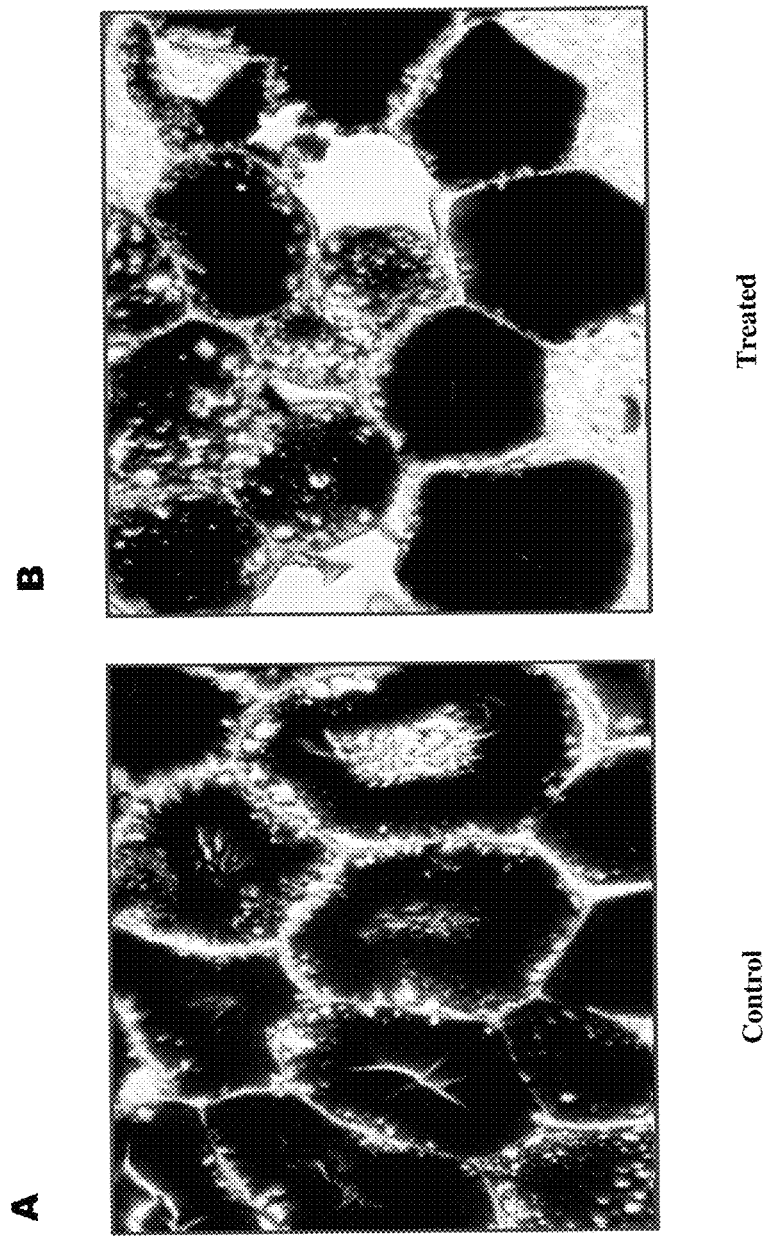
FIGS. 4A-4B show pictures of the suppressing effect of the composition of the present invention on hypertrophy of the subcutaneous adipocytes in obese mouse. A. Control. B. Treated.

As shown in the FIG. 4, adipocytes of control group became hypertrophic, compared to treatment group and the sizes of adipocytes were calculated with image analyzer to find out that the sizes have considerably decreased from 11.2±2.9 to 6.1±1.5 by 46%.

Figure 5:
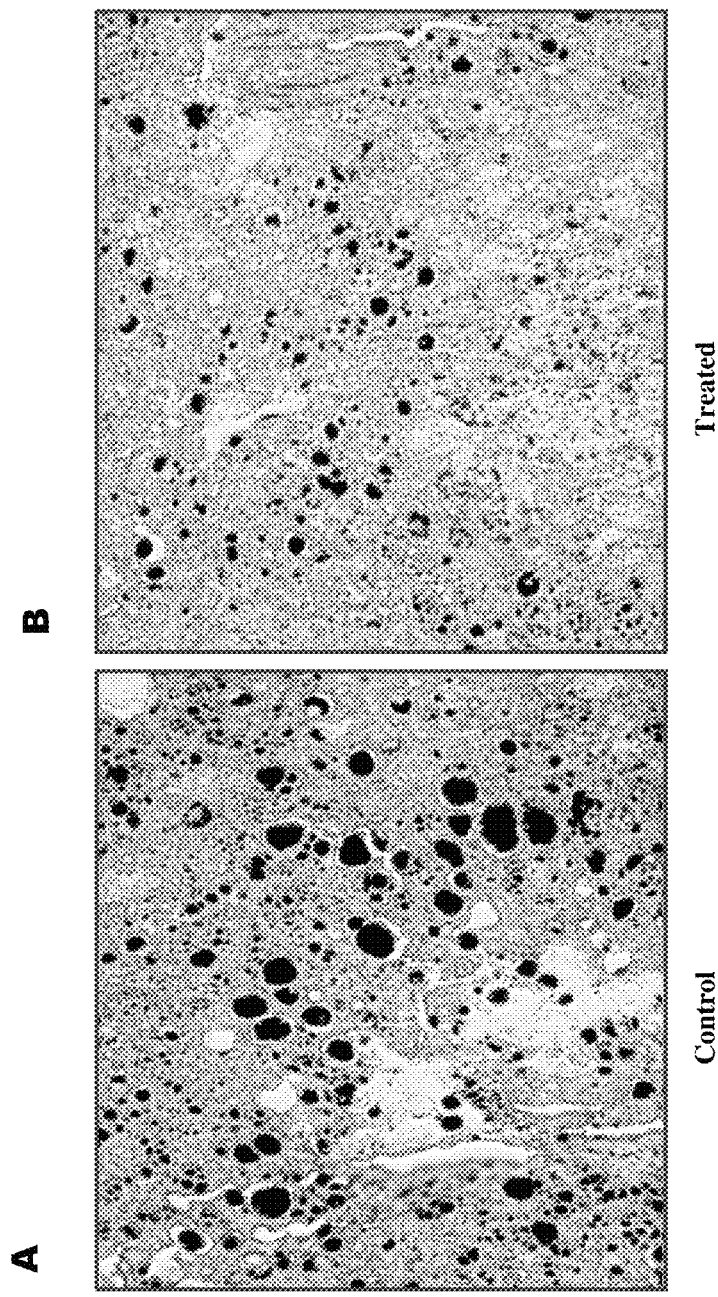
FIGS. 5A-5B show pictures of the reductive effect of the composition of the present invention on lipid accumulation in the liver of genetically obese mouse. Lipid vacuoles in liver. A. Control. B. Treated.
Figure 6:
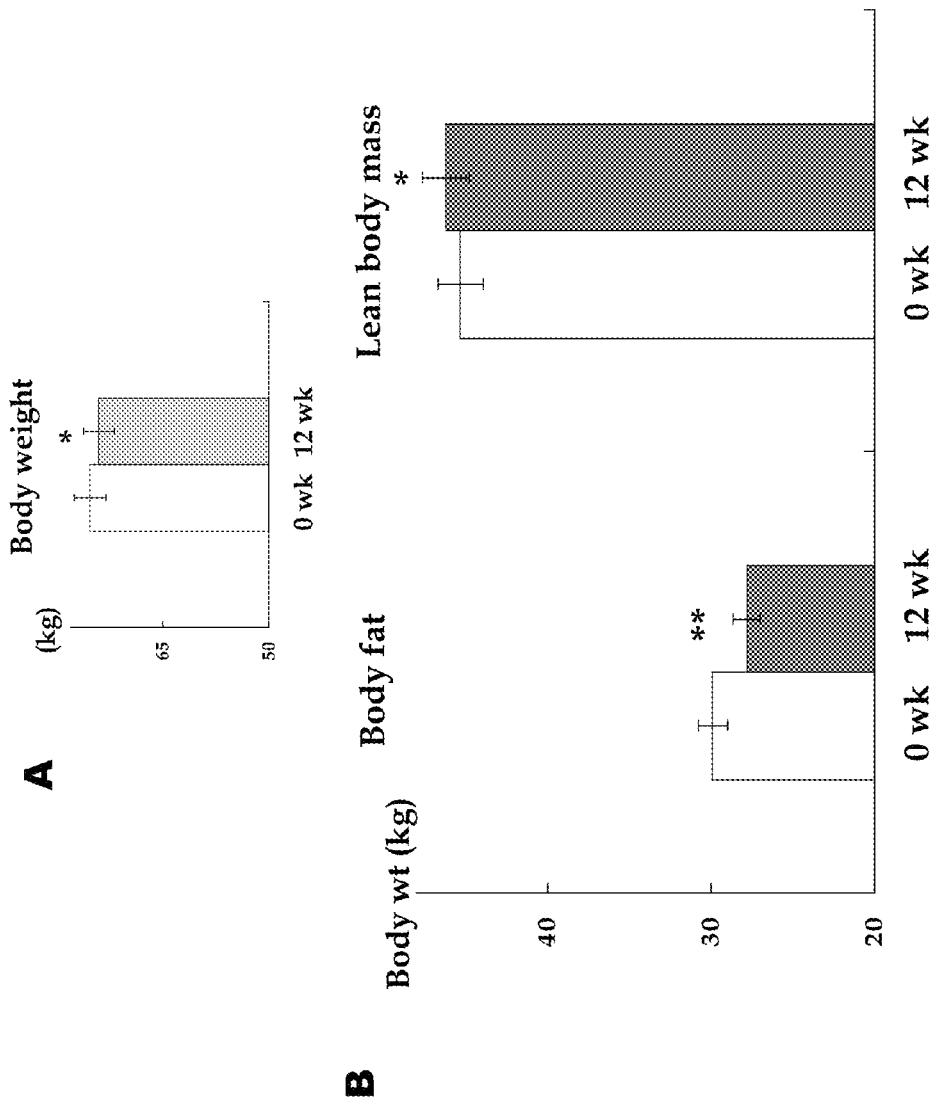
FIGS. 6A-6B show graphs of changes of A. body weight, and B. body fat, lean body mass in human subjects of the clinical trial before and after administration of the composition of the present invention. *p<0.05, **p<0.01 compared with 0 week value.

In addition, the size and number of black lipid vacuoles in the liver stained by osmium tetroxide were significantly decreased in the treatment group compared to control group as shown in the FIG. 5. The area of lipid vacuoles was remarkably reduced from 5.4±0.5 to 0.92±0.1 by 83% (Table. 3), which verified that sample 3 suppressed fat accumulation in the liver.

TABLE 3

Effect of sample 3 on the size of adipocytes and lipid vacuoles

|  | Control group | Treatment group | Reduction rate |
|---|---|---|---|
| Adipocytes (area, a.u.) | 11.2 ± 2.9 | 6.1 ± 1.5 | 46% |
| Lipid vacuoles (% area) | 5.4 ± 0.5 | 0.92 ± 0.1 | 83% |

Accordingly, the present composition was approved to have antiobesity effects to reduce the size of adipocytes, and lipid accumulation in the liver.

Therefore, the present composition can be usefully applied as an antiobesity composition to suppress body weight gains and body fat increase.

Experimental Example 4

Clinical Trial on the Antiobesity Effect of the Present Composition

The antiobesity effects of the present composition have been verified via clinical trial.

4-1. Collection of Human Subjects and Trial Method

Human subjects were publicly collected from volunteers aged 19-60 years with PIBW (Percent Ideal Body Weight) over 110% or abdominal obesity with waist circumference greater than 90 cm for men and 80 cm for women.

Any volunteers who had serious disease history, uncontrollable medium/high blood pressure, or thyroid disease, or were in the current course of treatment for disease, in pregnancy, planning to get pregnant or during lactation period, diagnosed as diabetes and treated with drug therapy, or taking drug that can affect their body weight (Xenical, Reductil, Deuretics, antidepressants, appetite-suppressants, etc.), employees of AngioLab, Inc., research participants and students, and their acquaintances were excluded.

In this pilot study, only trial group was included to evaluate the effect before and after intervention, without placebo group. A total of 25 subjects participated in the trial for 12 weeks and the result was processed with statistical analysis (Table. 4).

Each subject had taken two capsules that contained 250 mg of sample 3 three times a day for 12 weeks.

The male-female ratio of those who completed the 12-week trial was 3:22, their average age was 31.8±1.51 (19-47), average PIBW 133.3±3.17%, average body mass index (BMI) 28.4±0.67 kg/m$^2$ (23.5-34.7), and average body fat 39.4±1.46%. In addition, the rates of current smokers and drinkers were 20% and 72% respectively.

4-2. Changes in Anthropometric Parameters and Blood Pressure

As shown in the Table 4, when this research started, the mean body weight was 75.2±2.11 kg and, after 12 weeks, it decreased to 74.0±2.18 kg (p<0.05), which presented the statistical significance for decrease in both mean PIBW and mean BMI.

The body fat decreased from 39.4±1.46% to 37.2±1.38% (p<0.01) after 12 weeks while the lean body mass increased from 45.3±1.40 kg to 46.2±1.40 kg (p<0.05), which approves the considerable improvement of body composition (Tab. 6).

The mean waist circumference decreased to some extent after 12 weeks, and the hip circumference significantly reduced (p<0.01). In addition, mean diastolic blood pressure increased within normal range after 12 weeks (p<0.01).

TABLE 4

Changes of Anthropometric parameters and blood pressure before and after administration of the present composition

|  | Subject(n = 25) | |
|---|---|---|
|  | 0 week | 12 week |
| male/female | 3/22 | |
| age (year) | 31.8 ± 1.51 | |
| height (cm) | 162.8 ± 1.31 | |
| body weight (kg) | 75.2 ± 2.11 | 74.0 ± 2.18* |
| PIBW (%) | 133.3 ± 3.17 | 131.2 ± 3.40* |

TABLE 4-continued

Changes of Anthropometric parameters and blood pressure before and after administration of the present composition

| | Subject(n = 25) | |
|---|---|---|
| | 0 week | 12 week |
| BMI (kg/m$^2$) | 28.4 ± 0.67 | 27.9 ± 0.72* |
| body fat (%) | 39.4 ± 1.46 | 37.2 ± 1.38** |
| lean body mass (kg) | 45.3 ± 1.40 | 46.2 ± 1.40* |
| waist circumference (cm) | 91.4 ± 1.73 | 90.0 ± 1.78 |
| hip circumference (cm) | 104.9 ± 1.44 | 103.6 ± 1.47** |
| waist/hip ratio | 0.87 ± 0.01 | 0.86 ± 0.01 |
| tricep skinfold thickness (mm) | 26.1 ± 1.32 | 26.2 ± 0.91 |
| systolic blood pressure (mmHg) | 125.3 ± 3.38 | 124.2 ± 2.64 |
| diastolic blood pressure (mmHg) | 77.5 ± 2.09 | 82.2 ± 2.46** |
| current smoker (n(%)) | | 5 (20) |
| tabacco (cigarettes/day) | | 7.70 ± 3.03 |
| current drinker (n(%)) | | 18 (72) |
| alcohol intake (g/day) | | 8.82 ± 2.72 | mean ± S.E.
*p < 0.05,
**p < 0.01 compared with 0 week value 4-3. Changes in Fat and Muscle Areas Analyzed by CT Scanner The changes in fat and muscle areas at four different levels of body before and after administration of the present composition were analyzed by computed tomography (CT).

Figure 7:
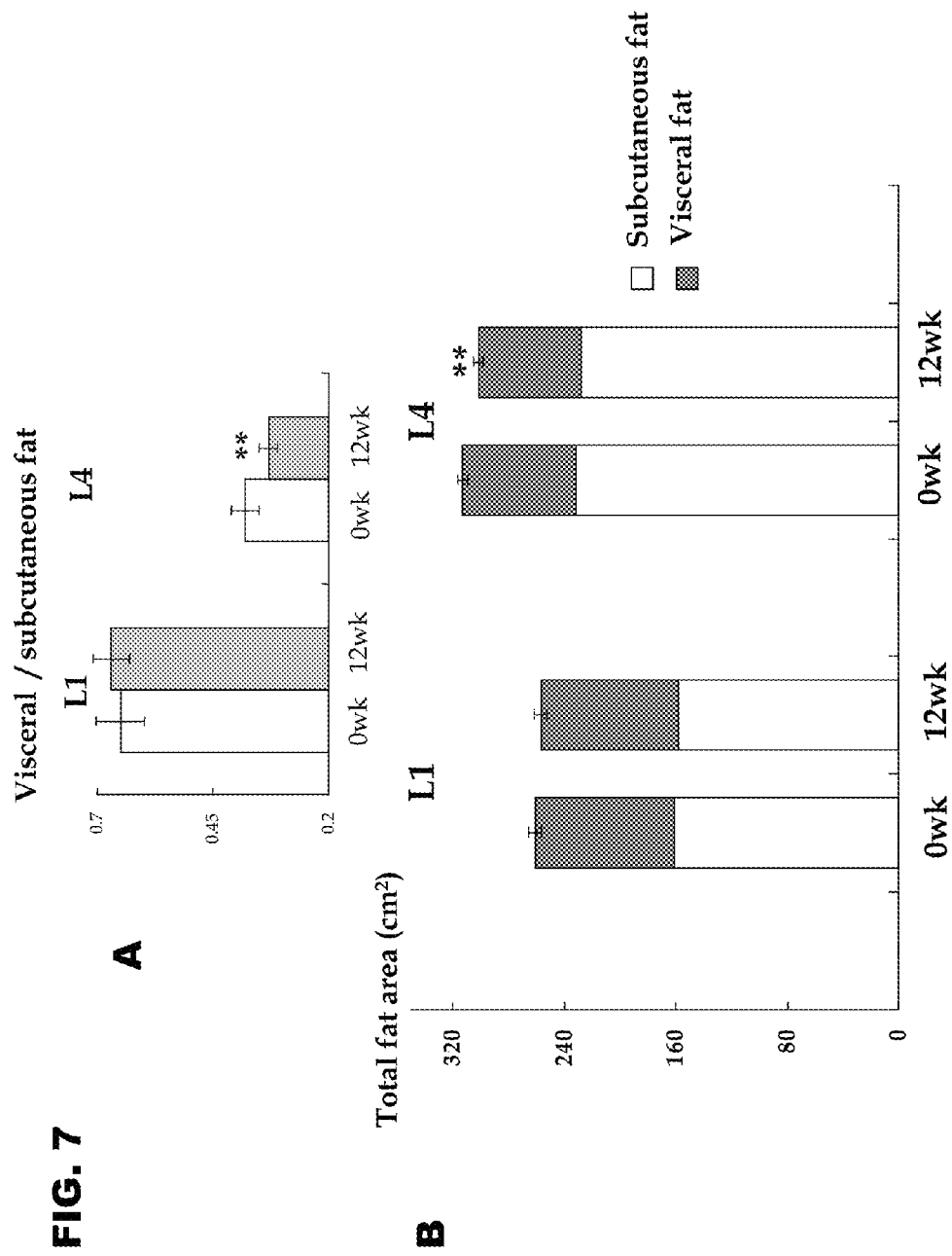
FIGS. 7A-7B show graphs of changes of A. visceral fat and subcutaneous fat, and B. total fat in human subjects of the clinical trial before and after administration of the composition of the present invention. **p<0.01 compared with 0 week value.

As shown in the Table 5, the fat in the upper abdomen scanned at first lumbar vertebra by CT did not show any significant change, but the fat in the lower abdomen scanned at fourth lumbar vertebra by CT was decreased. Visceral fat area was significantly decreased by 9.5% (p<0.01), and the ratio of visceral fat and subcutaneous fat was critically decreased (p<0.01) (FIG. 7, Table 5).

TABLE 5

Changes in fat and muscle areas at four different levels of body

| | Subject(n = 25) | |
|---|---|---|
| | 0 week | 12 week |
| 1st lumbar vertebra (upper abdomen) | | |
| total fat (cm$^2$) | 260.9 ± 13.1 | 256.6 ± 12.2 |
| visceral fat (cm$^2$) | 99.4 ± 6.54 | 98.7 ± 5.59 |
| subcutaneous fat (cm$^2$) | 161.5 ± 9.66 | 157.9 ± 9.43 |
| visceral fat/subcutaneous fat (ratio) | 0.65 ± 0.05 | 0.67 ± 0.05 |
| 4th lumbar vertebra (lower abdomen) | | |
| total fat (cm$^2$) | 313.0 ± 11.7 | 301.6 ± 13.4 |
| visceral fat (cm$^2$) | 81.5 ± 4.40 | 73.8 ± 4.72** |
| subcutaneous fat (cm$^2$) | 231.5 ± 11.4 | 227.8 ± 11.5 |
| visceral fat/subcutaneous fat (ratio) | 0.38 ± 0.03 | 0.33 ± 0.02** |
| mid thigh | | |
| fat (cm$^2$) | 87.7 ± 4.83 | 85.2 ± 4.64 |
| muscle (cm$^2$) | 113.8 ± 3.36 | 115.5 ± 3.81 |
| calf | | |
| fat (cm$^2$) | 29.8 ± 1.84 | 30.1 ± 2.00 |
| muscle (cm$^2$) | 73.4 ± 2.84 | 72.9 ± 3.31 | mean ± S.E.
**p < 0.01 compared with 0 week value 4-4. Changes in the Concentration of Serum Lipid, Lipoprotein, Fasting Plasma Glucose, and Insulin As shown in the Table 6, there were no changes in the concentration of triglyceride, total cholesterol, LDL choles terol, and HDL cholesterol, but apolipoprotein B decreased considerably (p<0.05).

However, there was considerable reduction in the ratio of total cholesterol/HDL cholesterol (p<0.05) and the ratio of LDL cholesterol/HDL cholesterol (p<0.05) (Table 6), demonstrating a significant improvement in atherogenic index (p<0.05).

TABLE 6

Changes in serum concentrations of lipid, apolipoprotein and fasting glucose level before and after administration of the present composition

| | Subject (n = 25) | |
|---|---|---|
| | 0 week | 12 week |
| triglyceride (mg/dl) | 124.9 ± 11.0 | 119.2 ± 10.7 |
| total cholesterol (mg/dl) | 203.3 ± 6.97 | 197.1 ± 6.36 |
| LDL cholesterol (mg/dl) | 126.7 ± 6.29 | 119.7 ± 5.99 |
| HDL cholesterol (mg/dl) | 51.6 ± 2.21 | 53.6 ± 2.38 |
| atherogenic index[1] | 3.10 ± 0.21 | 2.82 ± 0.18* |
| total cholesterol/HDL cholesterol | 4.10 ± 0.21 | 3.82 ± 0.18* |
| LDL cholesterol/HDL cholesterol | 2.57 ± 0.16 | 2.33 ± 0.15* |
| apolipoprotein A1(mg/dl) | 146.7 ± 4.24 | 142.1 ± 3.93 |
| apolipoprotein B(mg/dl) | 81.6 ± 3.80 | 75.4 ± 3.23* |
| blood sugar (mg/dl) | 91.6 ± 3.33 | 92.5 ± 3.96 |
| insulin (μIU/ml) | 12.4 ± 1.10 | 11.7 ± 1.30 |
| free fatty acid (μEq/L) | 499.7 ± 27.8 | 431.6 ± 42.2 | atherogenic index[1] = (total cholesterol − HDL cholesterol)/HDL cholesterol
mean ± S.E.
*p < 0.05 compared with 0 week value 4-5. Changes in the Concentration of Serum, GOT, GPT, BUN and Creatinine, Hemoglobin, and Thrombocyte The concentrations of GOT and GTP which are liver function indexes, and the concentrations of BUN and creatinine which are kidney function indexes were within normal range and had no changes after taking the formulation of this invention as shown in the Table 7.

However, the levels of red blood cells (p<0.05) and white blood cells (p<0.001) were increased within the normal range after 12 weeks. There was no change observed in the concentrations of hemoglobin and hematocrit, and the number of thrombocyte (Table 7).

TABLE 7

Changes of biochemical values before and after administration of the present composition

| | Subject (n = 25) | |
|---|---|---|
| | 0 week | 12 week |
| GOT (U/L) | 19.3 ± 0.99 | 21.5 ± 1.34 |
| GPT (U/L) | 18.4 ± 2.44 | 20.7 ± 2.57 |
| BUN (mg/dl) | 12.6 ± 01.52 | 11.7 ± 0.49 |
| creatinine (mg/dl) | 0.52 ± 0.03 | 0.52 ± 0.03 |
| white blood cells (×10$^3$/μl) | 4.92 ± 0.29 | 6.38 ± 0.26*** |
| red blood cells (×10$^6$/μl) | 4.48 ± 0.14 | 4.73 ± 0.11* |
| hemoglobin (g/dl) | 13.2 ± 0.47 | 13.7 ± 0.38 |
| hematocrit (%) | 38.7 ± 1.38 | 40.0 ± 1.11 |
| thrombocyte (×10$^3$/μl) | 306.0 ± 17.3 | 310.0 ± 13.5 | mean ± S.E.
*p < 0.05,
***p < 0.001 compared with 0 week value 4-6. Analysis of Meal Intake and Energy Expenditure The Table 8 shows that there were no significant differences between 0 week and 12 week values of meal intake, nutrient intake, and energy expenditure.

TABLE 8

Daily calorie intake and total energy expenditure

| | subject(n = 25) | |
|---|---|---|
| | 0 week | 12 week |
| TEE[1] | 2029.8 ± 36.6 | 2012.9 ± 38.2 |
| TCI[2] | 2352.3 ± 43.9 | 2325.0 ± 45.4 |
| TEE/TCI | 0.86 ± 0.11 | 0.87 ± 0.12 |
| carbohydrates (% of TCI) | 62.5 ± 0.43 | 62.1 ± 0.26 |
| proteins (% of TCI) | 17.2 ± 0.33 | 16.9 ± 0.27 |
| fats (% of TCI) | 20.6 ± 0.38 | 21.1 ± 0.44 |
| cholesterol (mg) | 425.8 ± 41.7 | 435.8 ± 33.3 |

TEE[1] = total energy expenditure
TCI[2] = total calorie intake
mean ± S.E.
No particular changes between 0 week and 12 week values.

4-7. Changes in the Concentration of Oxidized LDL and Lipid Peroxides

There was no change in the concentration of oxidized LDL, MDA which is lipid peroxide in blood, and 8-epi-PGF2α which is lipid peroxide in urine after taking the present composition (Table. 9).

TABLE 9

Changes in the concentration of oxidized LDL and lipid peroxides

| | Subject (n = 25) | |
|---|---|---|
| | 0 week | 12 week |
| LDL oxidation | | |
| Oxidized LDL (U/L) | 37.2 ± 1.99 | 36.5 ± 2.17 |
| lipid peroxidation | | |
| MDA (nmol/mml) | 3.15 ± 0.29 | 2.92 ± 0.17 |
| PGF2α (pg/mg creatinine) | 1391.2 ± 145.8 | 1125.2 ± 180.9 | mean ± S.E.
No particular changes between 0 week and 12 week values.

4-8. Status of Abnormal Response

No abnormal response was observed related to intake of sample 3 in 25 subjects who participated in this clinical trial.

INDUSTRIAL APPLICABILITY

As described above, the present compositions reduce body weight and body fat. The present compositions reduce blood cholesterol level and obesity-related blood glucose level.

In addition, the present compositions suppress hypertrophy of adipocytes, and the accumulation of lipid in the liver by reducing the size and number of lipid vacuoles.

In human clinical trial, the present compositions show that body weight, PIBW, body fat, especially visceral fat, apolipoprotin B concentration, the ratio of total cholesterol/HDL cholesterol and the ratio of LDL cholesterol/HDL cholesterol are significantly decreased, and atherogenic index are improved and muscle mass are increased.

Therefore, the present compositions can be usefully applied as antiobesity composition for reduction of body weight and suppression of abdominal fat, particularly, visceral fat.

The invention claimed is:

1. A method of suppressing obesity which comprises administering an antiobesity effective amount of a composition comprising *Melissa* extract, *Mori Folium* extract, and *Artemisia* extract, as active ingredients to a subject in need thereof, wherein the *Melissa* extract is in an amount of 0.1-99 parts by weight, the *Artemisia* extract is in an amount of 0.1-99 parts by weight, and the *Mori Folium* extract is in an amount of 0.1-99 parts by weight, with respect to 100 parts by weight of the composition.

2. The method according to claim 1, where the amount of *Melissa* extract, the *Artemisia* extract and the *Mori Folium* extract are in a ratio of 1-3:0.1-1:1-3 by dry weight.

3. The method of claim 1, wherein the composition further comprises at least one of dietary fiber, green tea or ginseng.

4. The method of claim 3, wherein the dietary fiber is at least one of *Psyllium* husk, cellulose, hemicellulose, crystalline cellulose, lignin, pectin, alginic acid, polymanuronic acid, guar gum, arabia gum, arabinogalactan, Konjak mannan, inulin, levan, polydextrose and indigestible maltodextrin.

5. The method of claim 3, wherein green tea is green tea powder, green tea extraction liquid or powder of green tea extraction liquid.

6. The method of claim 3, wherein ginseng is ginseng powder, ginseng extraction liquid or powder of ginseng extraction liquid.

7. A method for decreasing body fat mass comprising administering a therapeutically effective amount of a composition comprising *Melissa* extract, *Mori Folium* extract, and *Artemisia* extract, as active ingredients to a subject in need thereof, wherein the *Melissa* extract is in an amount of 0.1-99 parts by weight, the *Artemisia* extract is in an amount of 0.1-99 parts by weight and *Mori Folium* extract is in an amount of 0.1-99 parts by weight, with respect to 100 parts by weight of the composition.

8. The method according to claim 7, where the *Melissa* extract, the *Artemisia* extract, and the *Mori Folium* extract are in a ratio of 1-3:0.1-1:1-3 by dry weight.

9. The method of claim 7, wherein the composition further comprises at least one of dietary fiber, green tea or ginseng.

10. The method of claim 9, wherein the dietary fiber is at least one of *Psyllium* husk, cellulose, hemicellulose, crystalline cellulose, lignin, pectin, alginic acid, polymanuronic acid, guar gum, arabia gum, arabinogalactan, Konjak mannan, inulin, levan, polydextrose and indigestible maltodextrin.

11. The method of claim 9, wherein green tea is green tea powder, green tea extraction liquid or powder of green tea extraction liquid.

12. The method of claim 9, wherein ginseng is ginseng powder, ginseng extraction liquid or powder of ginseng extraction liquid.

* * * * *